(12) United States Patent
Filpula et al.

(10) Patent No.: US 7,642,072 B2
(45) Date of Patent: Jan. 5, 2010

(54) OPTIMIZED INTERFERON-BETA GENE

(75) Inventors: David Ray Filpula, Piscataway, NJ (US); Amartya Basu, East Hanover, NJ (US)

(73) Assignee: Enzon Pharmaceuticals, Inc., Bridgewater, NJ (US)

( * ) Notice: Subject to any disclaimer, the term of this patent is extended or adjusted under 35 U.S.C. 154(b) by 0 days.

(21) Appl. No.: 11/571,479

(22) PCT Filed: Jul. 26, 2005

(86) PCT No.: PCT/US2005/026883

§ 371 (c)(1),
(2), (4) Date: Jun. 5, 2007

(87) PCT Pub. No.: WO2006/015165

PCT Pub. Date: Feb. 9, 2006

(65) Prior Publication Data

US 2007/0259405 A1     Nov. 8, 2007

Related U.S. Application Data

(60) Provisional application No. 60/591,008, filed on Jul. 26, 2004.

(51) Int. Cl.
*C12P 21/04* (2006.01)
*C12N 15/63* (2006.01)
*C12N 1/21* (2006.01)
*C12N 15/00* (2006.01)
*C12P 21/00* (2006.01)
*C12N 15/11* (2006.01)
*C07H 21/04* (2006.01)
*C07K 14/00* (2006.01)

(52) U.S. Cl. ............... 435/71.2; 435/320.1; 435/252.3; 435/69.1; 435/70.1; 536/23.1; 536/23.52; 530/350

(58) Field of Classification Search .................. None
See application file for complete search history.

(56) References Cited

U.S. PATENT DOCUMENTS

| 4,588,585 A * | 5/1986 | Mark et al. ................ 424/85.2 |
| 2002/0172661 A1 | 11/2002 | Shirley et al. |
| 2004/0126361 A1 | 7/2004 | Saifer et al. |
| 2005/0008616 A1 * | 1/2005 | Nestaas et al. ............. 424/85.6 |

FOREIGN PATENT DOCUMENTS

| CA | 2416991 A1 | 7/2004 |
| WO | 2005084303 | 9/2005 |

OTHER PUBLICATIONS

Makrides. Microbiol Rev 60: 512-538, 1996.*
Grantham R. Trends Biochem Sc 5: 327-331, 1980.*
Cavnar, K. Master of Sc Thesis 2004.*
Maldonado et al. Biomol Engineer 24: 217-222, 2007.*
Stoletzki et al. Mol Biol Evol 24: 374-381, 2007.*

* cited by examiner

*Primary Examiner*—Jeffrey Stucker
*Assistant Examiner*—Aditi Dutt
(74) *Attorney, Agent, or Firm*—Lucas & Mercanti, LLP

(57) ABSTRACT

A new nucleic acid molecule that is codon-optimized to expressbeta interferon in *Escherichia coli* with greater efficacy.

11 Claims, 5 Drawing Sheets

FIG. 1

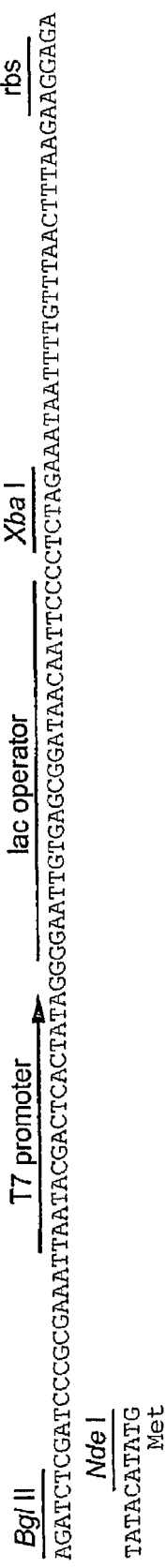

FIG. 3C

```
  Sal I    Hind III   Eag I                    Nhe I
                      Not I    Xho I
GTCGACAAGCTTGCGGCCGCACTCGAGATCAAACGGGCTAGCCAGGATCAAACTCGCCCCGAGAACTCGCCCCGAGAACCCCGAGGATGTCGAGCACCACCACCAGTGAGATCCGGCTG
Val AspLys Leu Ala Ala Ala LeuGlu Ile Lys Arg Ala Ser Gln Pro Leu Ala Pro Glu Asp Pro Glu Asp Pro Glu Asp Val Glu His His His His His His End
                                         Bpu1102 I                                                         HIS · Tag
                                                                                                                    BamH I  EcoR I  Sac I
                                                                                                                    GGATCCGAATTCGAGCTCC
                                                                                                                    Asp Pro Asn Ser Ser Ser
CTAACAAAGCCCGAAAGGAAGCTGAGTGGCTGCTGCCACCGCTGAGCAATAACTAGCATAACCCCTTGGGGCCTCTAAACGGGTCTTGAGGGGTTTTTG
                ← T7 terminator primer
                                   T7 terminator
```

Interferon-beta DNA Sequence and Sequencing Primer Locations

FIG. 4A

Comparison of Nucleotide Sequences between human native IFN-β-1b and its codon-optimized analogue for bacterial expression.

Identity between the two sequences is 74%

```
hNative:     1  atgagctacaacttgcttgattcctacaagaagcagcaatttcagagtcagaagctc    60
                ||||| || ||  || ||  ||  || ||  || || ||||| || |||||| ||
Optimized:   1  atgagttataacctgctggcttccaacgttctgcttcccaattcttcaatcgcaaaaactg  60 hNative:    61  ctgtgcaattgaatgggaggcttgaatactgcctcaaggacaggatgaacttgacatc   120
                || || |||||| || |||  || |||| ||||| ||||| ||||||||||  ||||
Optimized:  61  ctgtgccaacttaacggcgcctgaatattgttgaaagatcgcatgaacttgacatt   120 hNative:   121  cctgaggagattaagcagctgcagcagttccagaaggaggacgccgcattgaccatctat  180
                || || || |||||  || || || |||||  ||| |  ||  || |||||||| ||
Optimized: 121  ccggaagaaattaaacagctgcaacagttcaaaaaagaagatgccgcgttgaccatttac  180 hNative:   181  gagatgctccagaacatctttgctatttcagcagaagatttcatctagcactgctggaat  240
                ||||||| |||||||||||| ||||  |||| || ||  || || |  |||  ||||
Optimized: 181  gagatgctgcaaaacatttttcgccatcttcgccaagattcctccagtacggggtggaac  240 hNative:   241  gagactatttgttgagaacctcctgctaatgtctatcatcagataaaccatctgaagaca  300
                || ||| |||| || ||  |||| |||| ||||| ||||| |||| ||| |  ||||
Optimized: 241  gaaactattgtcgagaatttgctgctgaacgtgtatcaccaaattaatcatttgaaaacc  300
```

FIG. 4B

```
hNative:    301 gtcctgaagaaaaagaagagatttcaccaggggaaaactcatgagcagtctg 360
                || ||||||| ||||| |||||||||||| |||||||||||||| ||| |
Optimized:  301 gtgttggaagagaaactggaaaagagatttaccggggaaaactgatgtcaagcttg 360 hNative:    361 cacctgaaaagatattatgggaggattctgtcattacctgaaggccaaggagtacagtcac 420
                ||||||||| ||| || || ||| ||||| || |||||||||||||||| ||||||||||
Optimized:  361 catctgaaacgttactacggcgttactacggccgtatcctccactacctgaaagccaaagagtatagccac 420 hNative:    421 tgtgcctggaccatagtcagagtggaaatcctaaggaacttacttcattaacagactt 480
                || |||||||||||| || |||||| ||| |||||  ||||||| ||| ||  ||| ||
Optimized:  421 tgcgcctggacaattgttcgcgttgaaattctgcgtaacttttatttattaatcgtctc 480 hNative:    481 acaggttacctccgaaac 498
                || ||| ||||| || ||
Optimized:  481 accggctacctgcgcaat 498
```

SEQUENCE LISTING

```
<160> NUMBER OF SEQ ID NOS: 8

<210> SEQ ID NO 1
<211> LENGTH: 495
<212> TYPE: DNA
<213> ORGANISM: Artificial Sequence
<220> FEATURE:
<223> OTHER INFORMATION: Description of Artificial Sequence: Synthetic
      DNA sequence of the optimized gene encoding IFN-beta
      1b
<220> FEATURE:
<221> NAME/KEY: CDS
<222> LOCATION: (1)..(495)

<400> SEQUENCE: 1 agt tat aac ctg ctg ggc ttt ctg caa cgt tct tcc aat ttt caa tcg       48
Ser Tyr Asn Leu Leu Gly Phe Leu Gln Arg Ser Ser Asn Phe Gln Ser
  1               5                  10                  15 caa aaa ctg ctg tgg caa ctt aac ggg cgc ctg gaa tat tgc ttg aaa       96
Gln Lys Leu Leu Trp Gln Leu Asn Gly Arg Leu Glu Tyr Cys Leu Lys
             20                  25                  30 gat cgc atg aac ttt gac att ccg gaa gaa att aaa cag ctg caa cag      144
Asp Arg Met Asn Phe Asp Ile Pro Glu Glu Ile Lys Gln Leu Gln Gln
         35                  40                  45 ttt caa aaa gaa gat gcc gcg ttg acc att tac gag atg ctg caa aac      192
Phe Gln Lys Glu Asp Ala Ala Leu Thr Ile Tyr Glu Met Leu Gln Asn
     50                  55                  60 att ttc gcc atc ttt cgc caa gat tcc tcc agt acg ggg tgg aac gaa      240
Ile Phe Ala Ile Phe Arg Gln Asp Ser Ser Ser Thr Gly Trp Asn Glu
 65                  70                  75                  80 act att gtc gag aat ttg ctg gcg aac gtg tat cac caa att aat cat      288
Thr Ile Val Glu Asn Leu Leu Ala Asn Val Tyr His Gln Ile Asn His
                 85                  90                  95 ttg aaa acc gtg ttg gaa gag aaa ctg gaa aaa gag gat ttt acc cgg      336
Leu Lys Thr Val Leu Glu Glu Lys Leu Glu Lys Glu Asp Phe Thr Arg
            100                 105                 110 gga aaa ctg atg tca agc ttg cat ctg aaa cgt tac tac ggc cgt atc      384
Gly Lys Leu Met Ser Ser Leu His Leu Lys Arg Tyr Tyr Gly Arg Ile
```

-continued

```
              115                 120                 125
ctc cac tac ctg aaa gcc aaa gag tat agc cac tgc gcc tgg aca att    432
Leu His Tyr Leu Lys Ala Lys Glu Tyr Ser His Cys Ala Trp Thr Ile
        130                 135                 140 gtt cgc gtt gaa att ctg cgt aac ttt tat ttt att aat cgt ctc acc    480
Val Arg Val Glu Ile Leu Arg Asn Phe Tyr Phe Ile Asn Arg Leu Thr
145                 150                 155                 160 ggc tac ctg cgc aat                                                495
Gly Tyr Leu Arg Asn
                165

<210> SEQ ID NO 2
<211> LENGTH: 111
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 2
agatctcgat cccgcgaaat taatacgact cactataggg gaattgtgag cggataacaa    60
ttcccctcta gaaataattt tgtttaactt taagaaggag atatacatat g            111

<210> SEQ ID NO 3
<211> LENGTH: 513
<212> TYPE: DNA
<213> ORGANISM: Artificial Sequence
<220> FEATURE:
<223> OTHER INFORMATION: Description of Artificial Sequence: Synthetic
      DNA sequence of the optimized gene encoding IFN-beta 1b

<400> SEQUENCE: 3
catatgagtt ataacctgct gggctttctg caacgttctt ccaattttca atcgcaaaaa    60
ctgctgtggc aacttaacgg gcgcctggaa tattgcttga agatcgcat gaactttgac    120 attccggaag aaattaaaca gctgcaacag tttcaaaaag aagatgccgc gttgaccatt    180
tacgagatgc tgcaaaacat tttcgccatc tttcgccaag attcctccag tacggggtgg    240
aacgaaacta ttgtcgagaa tttgctggcg aacgtgtatc accaaattaa tcatttgaaa    300
accgtgttgg aagagaaact ggaaaaagag gattttaccc ggggaaaact gatgtcaagc    360
ttgcatctga acgttactac ggccgtatc ctccactacc tgaaagccaa agagtatagc    420
cactgcgcct ggacaattgt tcgcgttgaa attctgcgta acttttattt tattaatcgt    480
ctcaccggct acctgcgcaa ttaatgagga tcc                                513

<210> SEQ ID NO 4
<211> LENGTH: 232
<212> TYPE: DNA
<213> ORGANISM: Artificial Sequence
<220> FEATURE:
<223> OTHER INFORMATION: Description of Artificial Sequence: Synthetic
      DNA sequence of the optimized gene encoding IFN-beta
      1b
<220> FEATURE:
<221> NAME/KEY: CDS
<222> LOCATION: (2)..(118)

<400> SEQUENCE: 4 g gat ccg aat tcg agc tcc gtc gac aag ctt gcg gcc gca ctc gag atc    49
  Asp Pro Asn Ser Ser Ser Val Asp Lys Leu Ala Ala Ala Leu Glu Ile
  1               5                  10                  15 aaa cgg gct agc cag cca gaa ctc gcc ccg gaa gac ccc gag gat gtc      97
Lys Arg Ala Ser Gln Pro Glu Leu Ala Pro Glu Asp Pro Glu Asp Val
```

-continued

```
                    20                  25                  30
gag cac cac cac cac cac cac tgagatccgg ctgctaacaa agcccgaaag      148
Glu His His His His His His
          35 gaagctgagt tggctgctgc caccgctgag caataactag cataacccct tggggcctct  208 aaacgggtct tgagggtttt tttg                                        232
```

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

```
Asp Pro Asn Ser Ser Val Asp Lys Leu Ala Ala Ala Leu Glu Ile
 1               5                  10                  15

Lys Arg Ala Ser Gln Pro Glu Leu Ala Pro Glu Asp Pro Glu Asp Val
            20                  25                  30

Glu His His His His His His
          35
```

<210> SEQ ID NO 6
<211> LENGTH: 165
<212> TYPE: PRT
<213> ORGANISM: Artificial Sequence
<220> FEATURE:
<223> OTHER INFORMATION: Description of Artificial Sequence: Synthetic protein construct

<400> SEQUENCE: 6

```
Ser Tyr Asn Leu Leu Gly Phe Leu Gln Arg Ser Ser Asn Phe Gln Ser
 1               5                  10                  15

Gln Lys Leu Leu Trp Gln Leu Asn Gly Arg Leu Glu Tyr Cys Leu Lys
            20                  25                  30

Asp Arg Met Asn Phe Asp Ile Pro Glu Glu Ile Lys Gln Leu Gln Gln
        35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Asn Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
            100                 105                 110

Gly Lys Leu Met Ser Ser Leu His Leu Lys Arg Tyr Tyr Gly Arg Ile
        115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165
```

<210> SEQ ID NO 7
<211> LENGTH: 498
<212> TYPE: DNA
<213> ORGANISM: Homo sapiens -continued

```
<400> SEQUENCE: 7
atgagctaca acttgcttgg attcctacaa agaagcagca attttcagag tcagaagctc      60
ctgtggcaat tgaatgggag gcttgaatac tgcctcaagg acaggatgaa ctttgacatc     120
cctgaggaga ttaagcagct gcagcagttc cagaaggagg acgccgcatt gaccatctat     180
gagatgctcc agaacatctt tgctattttc agacaagatt catctagcac tggctggaat     240
gagactattg ttgagaacct cctggctaat gtctatcatc agataaacca tctgaagaca     300
gtcctggaag aaaaactgga gaagaagat ttcaccaggg gaaaactcat gagcagtctg      360
cacctgaaaa gatattatgg gaggattctg cattacctga aggccaagga gtacagtcac     420
tgtgcctgga ccatagtcag agtggaaatc ctaaggaact tttacttcat taacagactt     480
acaggttacc tccgaaac                                                  498

<210> SEQ ID NO 8
<211> LENGTH: 498
<212> TYPE: DNA
<213> ORGANISM: Artificial Sequence
<220> FEATURE:
<223> OTHER INFORMATION: Description of Artificial Sequence: Synthetic
      optimized DNA molecule

<400> SEQUENCE: 8
atgagttata acctgctggg ctttctgcaa cgttcttcca attttcaatc gcaaaaactg      60
ctgtggcaac ttaacgggcg cctggaatat tgcttgaaag atcgcatgaa ctttgacatt     120
ccggaagaaa ttaaacagct gcaacagttt caaaaagaag atgccgcgtt gaccatttac     180
gagatgctgc aaaacatttt cgccatcttt cgccaagatt cctccagtac ggggtggaac     240
gaaactattg tcgagaattt gctggcgaac gtgtatcacc aaattaatca tttgaaaacc     300
gtgttggaag agaaactgga aaagaggat tttacccggg gaaaactgat gtcaagcttg      360
catctgaaac gttactacgg ccgtatcctc cactacctga aagccaaaga gtatagccac     420
tgcgcctgga caattgttcg cgttgaaatt ctgcgtaact tttatttttat taatcgtctc     480 accggctacc tgcgcaat                                                  498
```

US 7,642,072 B2

OPTIMIZED INTERFERON-BETA GENE

BACKGROUND OF THE INVENTION

1. Field of the Invention

The present invention is directed to a new nucleic acid molecule that is codon-optimized to express beta interferon in *Escherichia coli* with greater efficacy.

2. Description of the Related Art

Many proteins or polypeptides are known that hold great promise for use in treating a wide variety of diseases or disorders. Interferons are relatively small polypeptide proteins which are secreted by most animal cells in response to exposure to a variety of inducers. Because of their antiviral, antiproliferative and immunomodulatory properties, interferons are of great interest as therapeutic agents. They exert their cellular activities by binding to specific membrane receptors on the cell surface. Once bound to the cell membrane, interferons initiate a complex sequence of intracellular events. In vitro studies demonstrated that these include the induction of certain enzymes, suppression of cell proliferation, immunomodulating activities such as enhancement of the phagocytic activity of macrophages and augmentation of the specific cytotoxicity of lymphocytes for target cells, and inhibition of virus replication in virus-infected cells. Thus, interferon proteins are functionally defined, and a wide variety of natural and synthetic or recombinant interferons are known. There are three major types of human interferons ("IFNs"). These are: Leukocyte IFN or IFN-alpha, a Type 1 IFN produced in vivo by leukocytes.

Fibroblast IFN or IFN-beta, a Type 1 IFN produced in vivo by fibroblasts.

Immune IFN or IFN-gamma, a Type 2 IFN produced in vivo by the immune system.

IFN-beta is of particular interest for the treatment of a number of diseases or disorders, and especially in the treatment of multiple sclerosis or MS. Natural human IFN-beta is a 166 amino acid glycoprotein, and the encoding gene has been sequenced by Taniguchi, et al. al., 1980, *Gene* 10: 11-15, and R. Derynck, et al., supra. Natural IFN-beta has three cysteine (cys) residues, located at amino acid positions 17, 31 and 141, respectively. In addition, numerous recombinant variants of IFN-beta are known.

Three recombinant IFN-beta products are licensed in Europe and the U.S. for treatment of MS. These are interferon beta-1a ("IFN-beta-1a ") or Avonex® (Biogen, Inc., Cambridge, Mass.), another IFN-beta-1a product marketed as Rebif® (Ares-Serono, Norwood, Mass.) and $Ser_{17}$ interferon-beta-1b ("IFN-beta-1b $_{Ser17}$") or Betaseron® (Berlex, Richmond, Calif.).

IFN beta-1a is produced in mammalian cells, e.g., Chinese Hamster Ovary ("CHO") cells using the natural human gene sequence, and the produced protein is glycosylated. See, for example, U.S. Pat. Nos. 5,795,779, 5,376,567 and 4,966,843, incorporated by reference herein. IFN beta-1b $Ser_{17}$ differs structurally from IFN-beta1a (Avonex® and Rebif®) because it is produced in *Escherichia coli* ("*E. coli*") using a modified human gene sequence having an engineered cysteine-to-serine substitution at amino acid position 17, so that the protein is non-glycosylated. See, e.g., U.S. Pat. Nos. 4,588,585 and 4,737,462, the disclosures of which are incorporated by reference herein.

Both Rebif® and Avonex® are stated by their package inserts to have specific activities, by differing methods, of at least $2-3\times10^8$ international units (IU)/mg. The Betaseron® package insert reports a specific activity of approximately $3\times10^7$ IU/mg, indicating a ten-fold difference in potency. While these activities are determined by somewhat different methods, the order of magnitude differences in antiviral and antitumor activities are also reflected in the recommended doses, which are measured in micrograms (60-130 mcg/week) for the Rebif® and Avonex® glycosylated IFN-beta 1a products, and from 0.25 milligrams and up for the non-glycosylated Betaseron® IFN-beta 1b.

IFN-beta, in each of its recombinant formulations, has multiple effects on the immune system, including the ability to inhibit viral replication. IFN-beta-1b is described by the manufacturer (Berlex, Richmond, Calif.) as enhancing suppressor T cell activity, reducing proinflamatory cytokine production, down-regulation of antigen presentation, and inhibition of lymphocyte trafficking into the central nervous system. Other sources have reported that IFN-beta reduces the production of IFN-gamma by T-lymphocytes. Other beneficial therapeutic effects are also suspected.

However, production of recombinant proteins in cell culture remains an expensive process. For this reason, there remains a longstanding and heretofore unsolved need in the art for significantly improved vectors and methods of producing IFN-beta compositions, particularly those containing IFN-beta 1b, particularly in non-mammalian cells.

SUMMARY OF THE INVENTION

The above-described needs are addressed, and other advantages are provided, by the nucleic acid molecule encoding IFN-beta-1b, that is described herein.

As a result of the present invention a vector and *E. coli* cell culture system is provided for economically producing IFN-beta-1b. The invention provides a nucleic acid molecule comprising the sequence of SEQ ID NO: 1, or its complement. The invention also provides an expression vector comprising the nucleic acid molecule of SEQ ID NO: 1, or its complement. The expression is optionally a plasmid or a bacterial phage, e.g., suitable for expressing the inventive nucleic acid molecule in *E. coli*.

The invention further provides a method of producing interferon beta 1b comprising culturing the above mentioned *Escherichia coli* host cell, and isolating interferon beta 1b produced by the host cell.

In addition, the invention provides an interferon beta protein produced by above mentioned method.

BRIEF DESCRIPTION OF THE DRAWINGS

FIG. 1 (SEQ ID NO: 1) illustrates the DNA sequence of the optimized gene encoding IFN-beta 1b (encoded protein is SEQ ID NO: 6).

FIG. 3A (SEQ ID NO: 2) illustrates the upstream control elements of Plasmid No. 1, including the BglII cleavage site, the location of the T7 promoter primer, the T7 promoter, the lac operator and the XbaI and NdeI sites, respectively (from 5' to 3').

FIG. 3B (SEQ ID NO: 3) illustrates the DNA sequence of the optimized gene encoding IFN-beta 1b in the context of Plasmid No. 1. From the 5' end is illustrated the same NdeI site noted in FIG. 3A, and the ATG Start codon (underlined), a primer 5600 sites, and the TAA TGA Stop codons, neither of which is shown in FIG. 1.

FIG. 3C (SEQ ID NO: 4) illustrates the elements downstream from the DNA sequence of the optimized gene encoding IFN-beta 1b, including Sal 1, HindIII, Eag I/NotI, XhoI, NheI, a herpes simplex virus (HSV) tag, His-Tag® Bpu1102I, the location of the T7 terminator primer and T7 terminator (encoded peptide is SEQ ID NO: 5).

FIG. 4A illustrates a comparison of the inventive optimized DNA molecule (SEQ ID NO: 8) to the native cDNA encoding IFN-beta 1b (SEQ ID NO: 7), through codon number 300.

FIG. 4B illustrates a comparison of the inventive optimized DNA molecule (SEQ ID NO: 8) to the native cDNA (SEQ ID NO: 7) encoding IFN-beta 1b, from codon number 301 through codon 498.

DETAILED DESCRIPTION OF THE INVENTION

Figure 1:
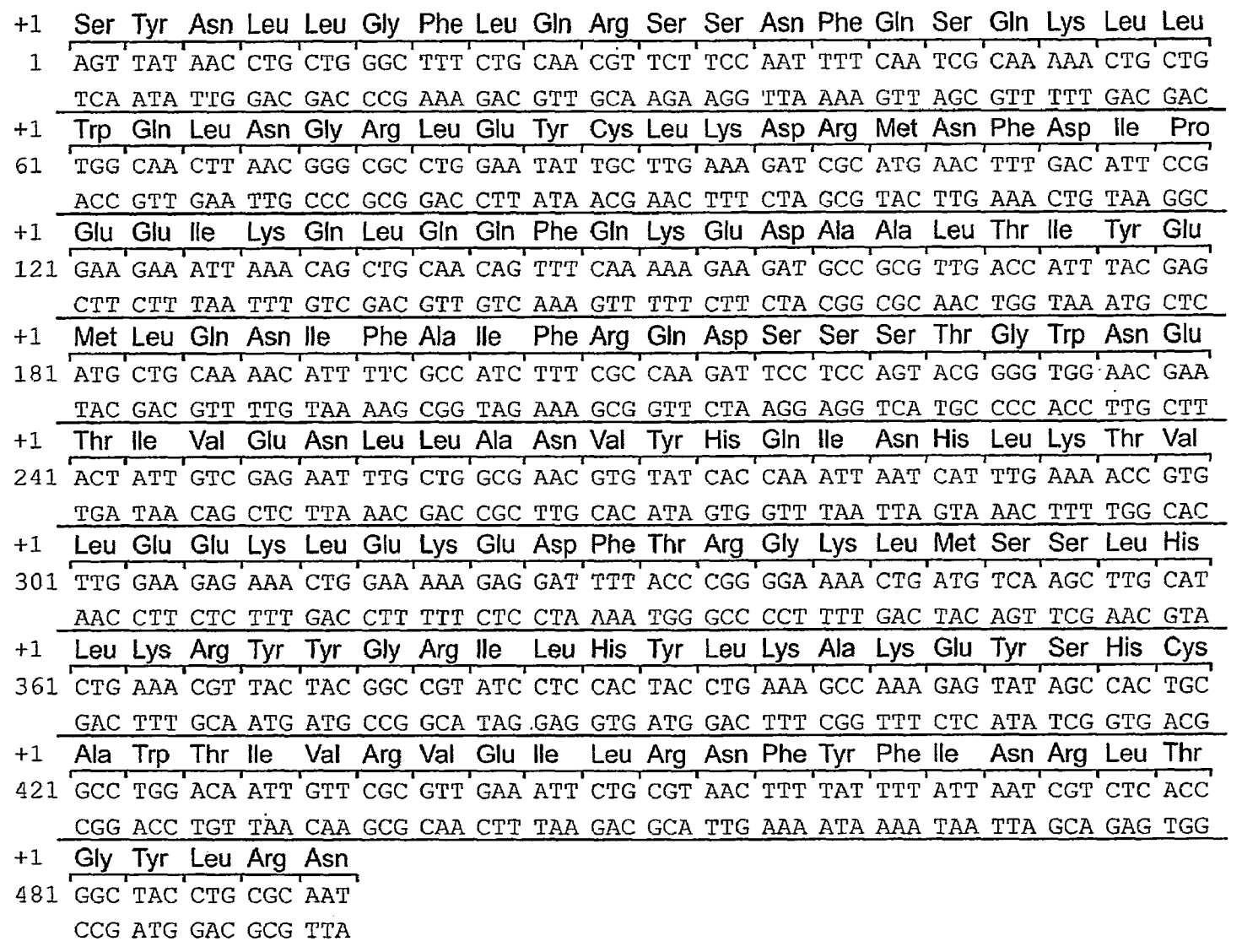
Figure 2:
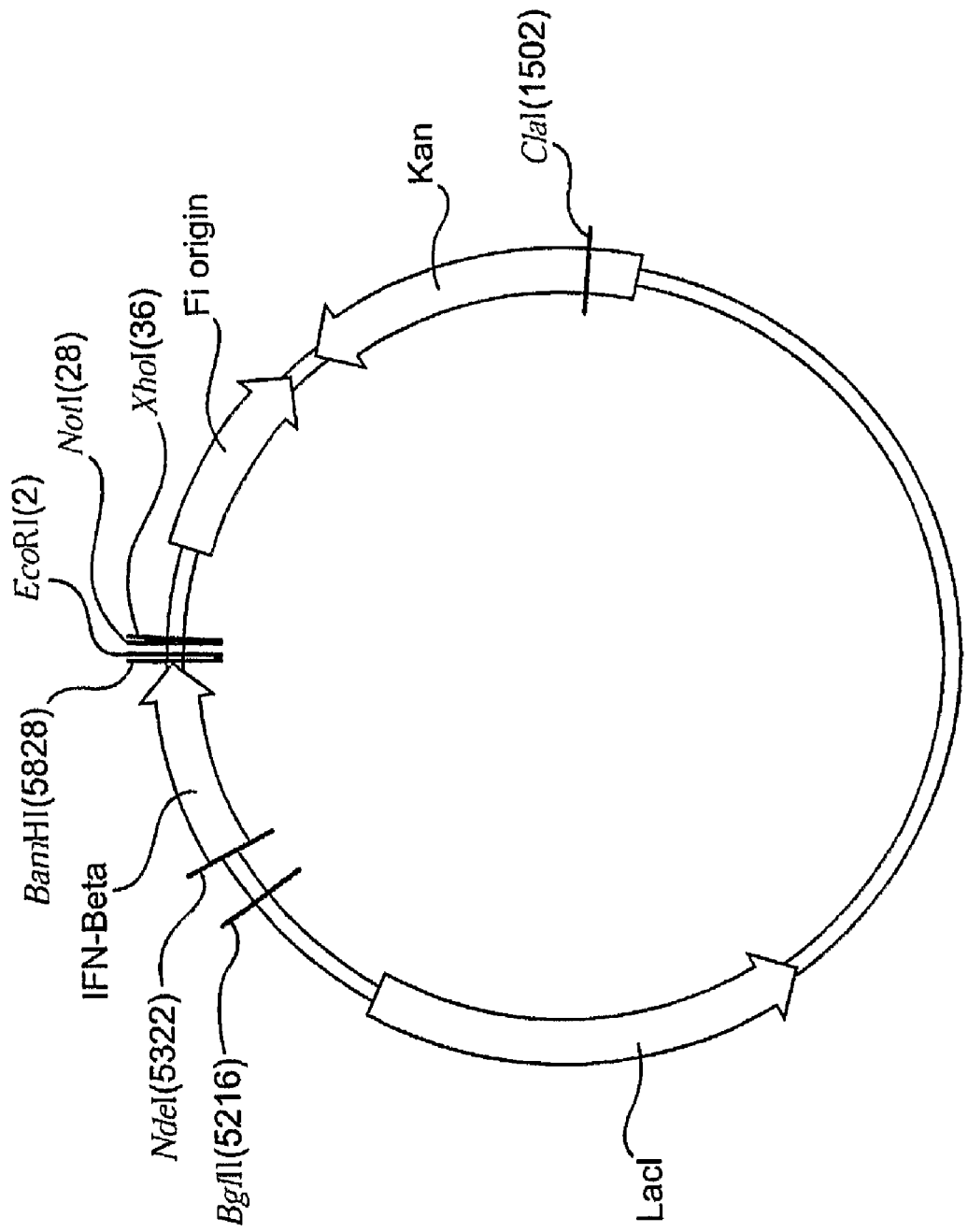
FIG. 2 illustrates Plasmid No. 1 employed to express the optimized gene in *E. coli*.

Accordingly, the invention provides a polynucleotide having the sequence illustrated by FIG. 1 (SEQ ID NO: 1), that differs from the polynucleotide previously employed to produce IFN-beta-1b (see, e.g., U.S. Pat. Nos. 4,588,585 and 4,737,462) in that various codons are optimized to provide significantly improved expression and/or protein production in E. coli.

A. Beta Interferons

The term "interferon-beta" or "IFN-beta" as used herein refers to IFN-beta isolated from natural sources and/or produced by recombinant DNA technology as described in the art, having sequence homology with, and the functionality, including bioactivity, of native IFN-beta. The term "interferon-beta 1b" or "IFN-beta 1b" as used herein refers to a mutein of IFN-beta having residue $Cys_{17}$ replaced by residue $Ser_{17}$, and expressed in a nonglycosylated form, with the N-terminal amino acid, Methionine, post-translationally removed.

Many muteins of the native human or animal IFN-beta are known and contemplated to be employed in the practice of the invention. Preferred muteins are described in greater detail by U.S. Pat. Nos. 4,588,585, 4,959,314; 4,737,462 and 4,450,103, incorporated by reference herein. In brief, as noted above, a preferred mutein is one wherein the $Cys_{17}$ residue of native human IFN-beta is replaced by serine, theonine, glycine, alanine, valine, leucine, isoleucine, histidine, tyrosine, phenylalanine, tryptophan or methionine. Most preferred is the non-glycosylated $Ser_{17}$ mutein of IFN-beta, also referred to herein as IFN-beta 1b.

Numerous methods of expressing and isolating IFN-beta proteins from host systems, and vectors suitable for expression by prokaryotic host cells, are known. For example, host systems include host cells selected from prokaryotic or eukaryotic host cells. Prokaryotic host cells include bacteria, such as Escherichia coli. Eukaryotic host cells include yeast cells, animal cells, e.g., in culture. The animal cells can include mammalian cells, such as primate or human cells, e.g., in culture, and optionally, human tissue cells, in vivo. Preferably, a mammalian host cell is a well characterized cell line adapted for continuous culture, such as a Chinese hamster ovary cell. Expression vectors suitable for expression in the selected host system are employed. Expression vectors include, for example, plasmid, bacterial phage, animal or plant virus, and/or other nucleic acid molecules suitable for replication in the selected host system.

For example, much of the IFN-beta employed in the examples provided hereinbelow was produced by the following method. A synthetic gene encoding an IFN-beta, e.g., IFN-beta 1b, was synthesized, following codon optimization for bacterial expression.

Other methods and reagents for IFN-beta production and purification are described, for example, by U.S. Pat. Nos. 6,107,057, 5,866,362, 5,814,485, 5,523,215, 5,248,769, 4,961,969, 4,894,334, 4,894,330, 4,748,234, 4,656,132, all incorporated by reference herein, as well as by other references too numerous to mention.

Methods of expressing and isolating IFN-beta proteins, and vectors suitable for expression by eukaryotic host cells, such as Chinese Hamster Ovary ("CHO") cells, are described in detail, e.g., by U.S. Pat. Nos. 4,966,843, 5,376,567, and 5,795,779, incorporated by reference herein.

B. Codon-Optimized Nucleic Acids

The use of the term "nucleic acid" herein encompasses both deoxyribonucleic acid (DNA) and ribonucleic acid (RNA) unless otherwise specified. It is art-known to optimize codons for expression and protein production in differing host organisms. It has been thought that the differences in the efficacy of expression in different host systems, by the same vector depends, among other factors, in the species of transfer RNA ("t-RNA") that might be present in the cytoplasm of different host cell types. For example, mammalian DNA generally encodes for the amino acid arginine with the codons AGA or AGG, but E. coli more reliably responds to codon triplets of CGX for encoding arginine.

Expression of eukaryotic gene products in prokaryotes is sometimes limited by the presence of codons that are infrequently used in E. coli. Expression of such genes can be enhanced by systematic substitution of the endogenous codons with codons over represented in highly expressed prokaryotic genes (Robinson et al., Nucleic Acids Res. 12:6663, 1984). Without being bound by any theology or hypothesis, it is commonly supposed that rare codons cause pausing of the ribosome, which leads to a failure to complete the nascent polypeptide chain and a uncoupling of transcription and translation. Pausing of the libosome is thought to lead to exposure of the 3' end of the mRNA to cellular ribonucleases. Optimizing a gene to more efficiently express in a different host organism is known, although it cannot be predicted in advance whether the changes so produced will have the desired positive improvement in expression and production of the targeted protein. These changes can be implemented using any art-known synthetic or biological procedure, such as by preparing synthetic oligonucleotides corresponding to IFN-beta 1b cDNA domains, with selected codons substituted therein, and then employing amplification methods, such as PCR, to insert the modified oligonucleotide into a target cDNA molecule. Preferably, the gene is synthesized de novo, by any art-standard method, to encode IFN-beta and/or IFN-beta 1b, using codons known to be optimally expressed by E. coli. More preferably, the gene is synthesized as a set of overlapping oligonucleotide segments, that are then assembled by standard methods into the completed optimized DNA molecule.

The modified gene of the present invention can be designed to encode IFN-beta, and particularly human IFN-beta, and most particularly, IFN-beta 1b, as described supra.

EXAMPLE

The following example serves to provide further appreciation of the invention but is not meant in any way to restrict the effective scope of the invention.

Example 1

Optimized DNA and Vector

The human interferon beta-1b sequence was optimized for bacterial expression by following the standard bacterial codon usage for Escherichia coli K12, using the codon data described by Grantham R. et al.; 1981; "Codon catalogue usage in genome strategy modulated for gene expressivity," *Nucleic Acid Res.*9:r43-r47, and Lathe, R. 1985; "Synthetic oligonucleotide probes deduced from amino acid sequence data, Theoretical and Practical considerations." *J. Mol Biol;* 183:1-12.

The corresponding RNA sequence was then analyzed for the formation of hairpin structure or loop formation and was subjected to minimum free energy calculations. The optimized cDNA sequence was further modified for four leucine residues, replacing TTA with CTG, at nucleotide positions 57, 81, 261, and 315, respectively. The leucine codon-modified sequence of interferon beta-1b was again subjected to minimum fee energy calculation and appeared to have very little free energy change compared to the initial optimization (−117.8 k Cal as opposed to −110.05 k Cal). The cDNA of interferon beta-1b encoding the reported 165 amino acid sequence of human IFN-beta 1b was then synthesized using standard chemical synthesis of overlapping oligonucleotide segments. The inventive DNA molecule can also be readily prepared by any other art-known methods, e.g., by employing PCR to insert segments with modified codons into the original reported cDNA encoding human IFN-beta 1b. The flanking restriction sites, NdeI and BamHI were included at the termini of the gene. Following digestion of the synthetic DNA with the restriction enzymes NdeI and BamHI, the 0.5 Kb gene was then ligated via T4 DNA ligase into the plasmid vector pET-27*b* (+) (from Novagen Corporation), which was also digested with these two enzymes. The recombinant plasmid was then introduced into *E. Coli* strain BLR (DE3) by electroporation using a BTX Electro Cell Manipulator 600 according to the manufacturer’s instructions. The transformation mixture was plated on LB agar plates containing kanamycin (15 micrograms per ml) to allow for selection of colonies containing the plasmid pET-27*b* (+)/IF-beta-1b (designated plasmid No. 1). Isolated colonies were further purified by plating and analyzed for IPTG inducible gene expression by standard methods, such as those described in Novagen pET System Manual, Ninth Edition.

The transformed host cells produced about 10 fold more IFN beta protein per batch than did the same type of host cells employing the previously available, non-optimized cDNA coding for IFN-beta.

A number of references are cited in the present patent application, all of which are incorporated herein by reference in their entireties.

We claim:

1. A recombinant nucleic acid molecule comprising the sequence of SEQ ID NO: 1 which encodes interferon beta 1b, or comprising the sequence complementary to that of SEQ ID NO: 1.

2. An expression vector comprising the nucleic acid molecule of claim 1.

3. The expression vector of claim 2 that is a plasmid or a bacterial phage.

4. A *Escherichia coli* comprising the expression vector of claim 2.

5. A method of producing interferon beta 1b comprising culturing the *Escherichia coli* host cell of claim 4, and isolating interferon beta 1b produced by the host cell.

6. The interferon beta protein produced by the method of claim 5.

7. The nucleic acid molecule of claim 1 comprising the sequence of SEQ ID NO: 1.

8. The nucleic acid molecule of claim 1 that is isolated.

9. The nucleic acid molecule of claim 1 that is a DNA.

10. The nucleic acid molecule of claim 1 that is an RNA.

11. A recombinant nucleic acid molecule consisting essentially of the nucleic acid molecule of SEQ ID NO: 1.

* * * * *